United States Patent [19]

Glickman

[11] Patent Number: 5,893,841
[45] Date of Patent: Apr. 13, 1999

[54] BALLOON CATHETER WITH OCCLUDED SEGMENT BYPASS

[75] Inventor: Morton Glickman, New Haven, Conn.

[73] Assignee: Delcath Systems, Inc., Stamford, Conn.

[21] Appl. No.: 08/708,046

[22] Filed: Aug. 30, 1996

[51] Int. Cl.$^6$ .................................................. A61M 29/00
[52] U.S. Cl. ........................... 604/101; 604/96; 606/194
[58] Field of Search .......................... 604/96, 101, 280, 604/282, 256, 246, 28, 22; 606/194, 159, 192, 193, 195

[56] References Cited

U.S. PATENT DOCUMENTS

| | | | |
|---|---|---|---|
| 5,135,484 | 8/1992 | Wright | 604/28 |
| 5,178,608 | 1/1993 | Winters | 604/101 X |
| 5,360,403 | 11/1994 | Mische | 604/101 |

*Primary Examiner*—John D. Yasko
*Attorney, Agent, or Firm*—Stephen E. Feldman

[57] ABSTRACT

An improved balloon catheter with an inferior vena cava blood shunt or bypass is provided. Posterior and anterior ports in the wall of the catheter connect to a common lumen within the catheter, forming a shunt or bypass for blood flowing in the blood vessel. The blood shunt or bypass spans the blockage in the blood vessel generated by enlargement of the balloons of the balloon catheter. Bypass port closure apparatus is provided which is operated at the external end of the catheter. The bypass port closure device functions to open and close at least one of the ports of the bypass, effectively opening and closing the bypass.

14 Claims, 2 Drawing Sheets

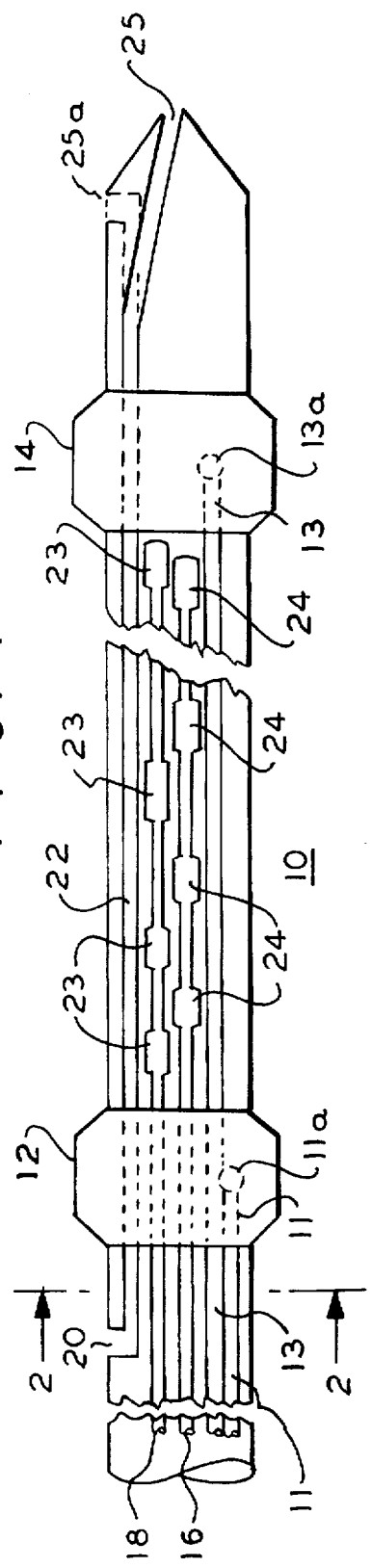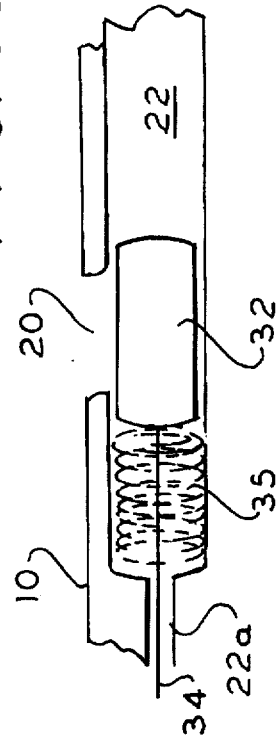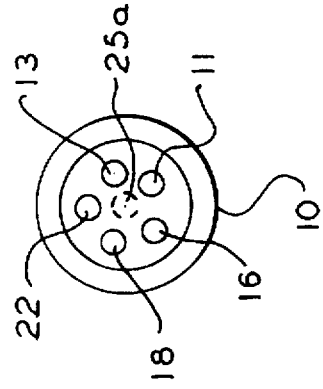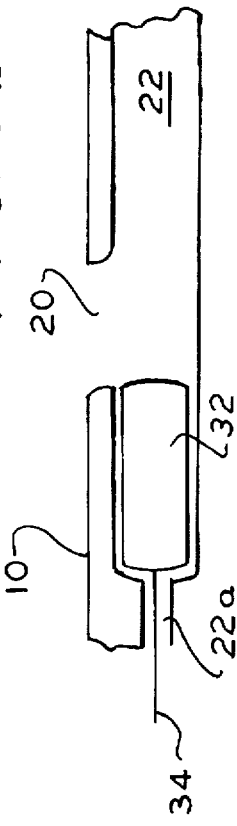

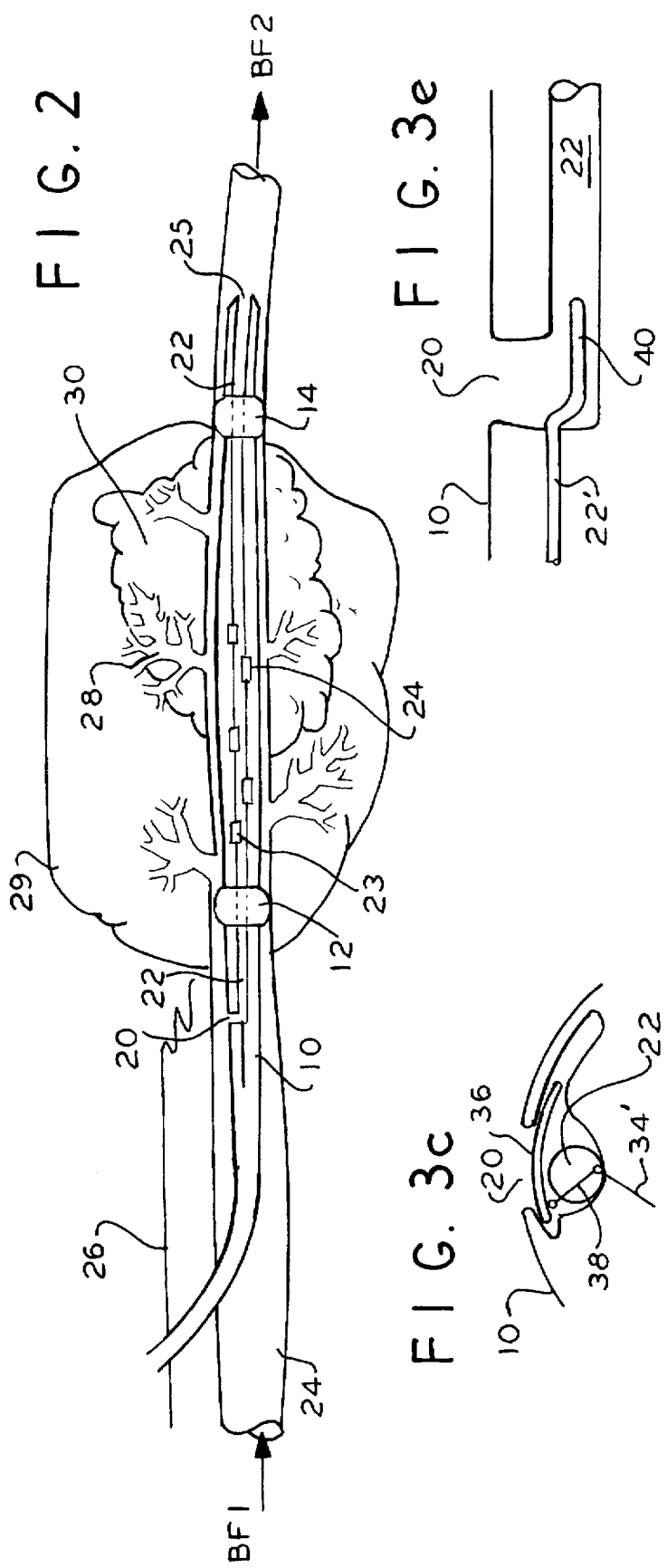

5,893,841

1

BALLOON CATHETER WITH OCCLUDED SEGMENT BYPASS

BACKGROUND OF THE INVENTION

1. Field of the Invention

The present invention relates to a catheter, used in medical procedures, which has one or more balloons. The catheter may be inserted into a body, particularly into a blood vessel of the body, for example. The balloon of the balloon catheter may then be enlarged, as by inflation, for example, for controlling the flow of blood in the blood vessel in which the balloon catheter is inserted. In particular the present invention is an improved balloon catheter which includes one or more inflatable balloons which are individually and separately operated, and a blood bypass or shunt for retaining blood flow through a vessel while the blood flow to and/or from a predetermined part or area of the body is shut-off or isolated by the balloons of the catheter.

2. Prior Art

The use of apparatus, in medical procedures, for controlling blood flow in a blood vessel and/or for isolating an organ or area of the body from blood flowing in a blood vessel is known and apparatus used for isolating an organ of the body or an area of the body from the blood carried in the blood vessel is taught in the prior art. One such apparatus is known as a catheter, specifically a balloon catheter. An example of some U.S. patents that teach apparatus for controlling blood flow in selected parts or areas of the body are:

U.S. Pat. No. 5,069,662 to Bodden 1991

U.S. Pat. No. 4,883,459 to Calderon 1989

U.S. Pat. No. 4,820,261 to Schmoll, et al 1989

U.S. Pat. No. 4,708,718 to Daniels 1987.

These prior art patents and some others which teach related apparatus and medical practices, teach isolation of predetermined or selected body organs and/or body areas by use of at least two spaced balloons on a catheter. The balloon catheter, such as taught in the prior art, may be used to achieve isolation of a body part from its blood supply. However, one of the problems attendant such a procedure is that although control of the blood flow through a portion of the blood vessel is achieved, including blockage of the blood supply to the selected body organ or body area, blood flow through the section of the blood vessel where the blockage is generated, is completely interrupted. This condition has been tolerated because when one blood vessel becomes blocked, for one reason or another, the body normally increases the blood flow through other, essentially paralleling blood vessels. However, the increase in blood flow in essentially paralleling vessels, under such circumstances may, at times, overload the blood vessels and should be avoided. The present invention addresses the problem of achieving isolation of a body part or body area from its normal blood supply through the use of a balloon catheter in the blood vessel, without generating complete blockage of the blood flow through the blood vessel.

SUMMARY OF THE INVENTION

The present invention provides an improved catheter, for use in the blood vessel system in the body, which catheter includes at least two spaced balloons capable of being enlarged, by inflation, for example, for generating a controlled blockage in the blood vessel, for cutting off the blood flow to a selected body part without totally interrupting the flow of blood through the blood vessel in which the con-

2 trolled blockage is generated. The improved catheter provides a shunt or bypass in the catheter that includes an opening or port in the wall of the catheter, upstream, in the direction of blood flow, from the upstream balloon and another opening or port in the wall of the catheter downstream, in the direction of blood flow, from the downstream balloon, with an internal lumen or channel in the catheter connected to both the upstream and the downstream ports. This structure provides a bypass or shunt for blood flowing in the blood vessel which is blocked by the inflated balloons of the catheter, permitting blood flow in the blocked blood vessel to bypass the blockage and the isolated organ or area, without the need to reroute blood to other blood vessels in the blood vessel network of the body.

The improved catheter also provides an adjustable means for opening and/or closing one or both bypass ports in the catheter wall for controlling the flow of blood through the bypass.

BRIEF DESCRIPTION OF THE DRAWINGS

FIG. 1 is a representation of part of an improved catheter on which the present invention is practiced;

FIG. 1a is a cross section view of the catheter of FIG. 1 along the line a—a;

FIG. 2 is a representation of the present improved catheter in place, in a blood vessel;

FIGS. 3a and 3b represent an apparatus for opening and closing ports, of the bypass in the catheter wall; and, FIGS. 3c and 3d and FIGS. 3e and 3f represent alternate apparatus for opening and closing ports, of the bypass in the catheter wall.

DETAILED DESCRIPTION OF THE INVENTION

Referring to FIG. 1, part of a balloon catheter 10 is represented with spaced balloons 12 and 14. Each balloon is connected to a separate lumen inside the wall or cover of the catheter. A lumen is a shaft or channel inside the catheter. FIG. 1a represents a cross section of the catheter along line a—a of FIG. 1 showing the catheter wall 10 and the lumens 11, 13, 16 and 18. The forward tip of the catheter is represented in broken line form.

Lumen 11 is connected to the balloon 12 and opens into the interior of the balloon, at 11a. The lumen 11 extends along the catheter to the external end (not shown) which is outside the body. A pump means (not shown) may be connected to the external end of the lumen 11, for expanding and contracting the balloon 12, as desired. Lumen 13 is connected to the balloon 14 and opens into the interior of the balloon, at 13a. The lumen 13 extends along the catheter to the external end (not shown) of the catheter, which is outside the body. A pump means (not shown) may be connected to the external end of lumen 13, for expanding and contracting the balloon 14, as desired. The use of separate lumens to connect the separate balloons to separate pump means is an improvement over the prior art which teaches the use of a common lumen and pump means for both balloons of the catheter. By having separate lumens connected to the respective balloons and separate pump means for inflation and deflation, for example, increased control over the blood flow to and/or from the isolated body part is achieved.

The lumens 16 and 18 are connected to ports 24 and 23 respectively, in the wall of the catheter, the ports being positioned in that part of the catheter wall which lies between the balloons 12 and 14. The lumens 16 and 18 each extend to the external end of the catheter and may be connected to means for injecting and/or to means for withdrawing fluids into and from the isolated area of the vessel.

The part of the catheter that is represented in FIG. 1 is that part of the catheter that is used for insertion into the body and particularly into the blood vessel of the body. Attention is also directed to FIG. 2, which represents the catheter of FIG. 1 inserted into the flesh 26 of a body and into the blood vessel 27, of such body. That particular portion of the catheter represented in FIG. 1 is positioned in that part or section of the blood vessel that passes through an organ 29. The balloons 12 and 14 are represented as enlarged, such as inflated, for example, effectively blocking the blood flowing through the vessel 27 and cutting of the blood supply to the network 28 of vessels in the organ 29.

If the vessel 27 were an artery, blood would be flowing in the direction of the arrow BF1 and part of the blood would flow from the vessel 27 into the vessel network 28 and thus into the organ 29, for example. According to the location of the organ in the body, blood not diverted to the vessel network 28 would continue along the vessel 27, as indicated by arrow BF2, to other organs and/or areas of the body.

If the vessel 27 were a vain, blood would be flowing from the organ 29, into the vessel network 28 and into the vessel 27, flowing in the direction of the arrow BF2. Depending on the location of the organ 29 in the body, blood from other organs and/or parts of the body may be flowing in the vessel 27, as indicated by the arrow BF1, for example.

If a blockage of the vessel 27 were generated by enlargement of the spaced balloons 12 and 14, such as by inflation, for example, while inside the blood vessel 27, the organ 29 will be isolated from the blood flow in the vessel.

The present invention provides a balloon catheter 10 which includes an opening or port 20 in the wall of the catheter, just upstream, in the direction of blood flow from the posterior balloon 12. The port 20 connects to a lumen 22, that extends toward the tip of the catheter, the other end of lumen 22 connects with a second opening or port 25 in the tip of the catheter, or in the wall of the catheter, just downstream from the forward or anterior balloon 14. The two ports 20 and 25 and the connecting lumen 22 form a shunt or bypass for the blood flowing through the vessel from the arrow BF1 to the arrow BF2, and blocked by the inflated balloons 12 and 14. With a blood bypass, such as shown and described as part of the balloon catheter, isolation of the body part from the blood supply in the vessel is achieved without interfering with the flow of blood through the blood vessel.

The port 25 is preferably positioned at the tip of the catheter, as represented in FIGS. 1 and 2, however, the anterior port may be in the wall of the catheter, as represented in broken line form in FIG. 1, at 25a.

The bypass of the occluded segment of the catheter may include one or more adjustable covers, which may be opened or closed, so as to open or close the port or ports of the bypass, as desired. By providing an adjustable hatch or cover for the port 20 and/or the port 25, control of the blood flow through the bypass is achieved. Examples of a cover or hatch that may be used to open and/or close of the port or ports 20 and 25 of the bypass are represented in FIGS. 3a through 3d, without limitation. It will be appreciated that by closing only one of the two ports of the bypass, the bypass is effectively closed.

Referring particularly to FIG. 2, part of a balloon catheter 10 is represented as inserted through the flesh 26 of a body and into a vessel 27. The catheter extends along the interior of the vessel to some desired position. In the representation it is assumed that the balloon catheter is used to isolate an organ of the body from the blood flow in the vessel. An organ 29 of the body is represented with a blood vessel 27 passing by or through the organ, part of the blood flowing through the vessel entering or coming from the vessel network 28.

Let it be assumed that the blood flow through the vessel 27 is in the direction of the arrows BF1 and BF2, and that the balloon catheter 10 is positioned inside the vessel 27 with the balloons 12 and 14 positioned so as to bracket the vessel network 28 of the organ 29. When the balloons 12 and 14 are enlarged so as to form a block in the vessel 27, the organ 29 will be isolated from both forward and reverse blood flow from the vessel. However, blood flow through the vessel 27 will continue by virtue of the open bypass provided. With the ports 20 and 25 open, blood flow of up to 500 ml per minute may flow through the bypass formed by the port 20, the lumen 22 and the port 25. Isolation of the organ from the blood flow in the vessel is established but blood flow through the vessel is maintained.

The ports 23, in the wall of the catheter are connected to the lumen 18 and the ports 24, in the wall of the catheter are connected to the lumen 16. The lumens 16 and 18 extend between the ports, at one end of the lumens to the external end of the catheter (not shown). Pump means (not shown) may be connected to each lumen, at the external end of the catheter, which may be used to inject and/or evacuate fluids into and/or from the occluded segment of the vessel, for example.

FIGS. 3a and 3b represent one embodiment of bypass port closure that may be used for opening and closing the port 20, for example. In order for the bypass to effectively function, both ports 20 and 25 must be open. Thus, by closing one of the ports of the bypass, for example, the port 20, the bypass, including the port 20, the lumen 22 and the port 25 may be effectively closed. FIG. 3a shows a piston 32 which is used to close the port 20, when in a forward or closed position. The piston 32 is connected to a lead 34 which extends, via a lumen 22a to the external part of the catheter. The lead 34 may be pulled, longitudinally, so as to move piston 32 from a closed position, such as represented in FIG. 3a to an open position, such as represented in FIG. 3b. When in a closed position, the piston 32 is in the lumen 22 and across the port 20, closing the port 20 and effectively closing the bypass.

The piston may include a biasing means, such as a spring 35, shown in broken line form, or other biasing member, so that when the lead 34 is released, the bias means 35 drives the piston forward, across the port 20, closing the port 20 and effectively closing the bypass.

FIGS. 3c and 3d show another embodiment of port closure, for closing and opening the port 20. FIG. 3c shows a hatch 36 in a closed position, closing the port 20. The hatch 36 may be moved in a clockwise direction, transversely of the length of the catheter, by a lever 38, connected to the lead 34'.

The lead 34' is connected at one of its ends to the base of lever 38, which is connected at its other end, to the hatch or cover 36. The lead 34' extends through the lumen 22a to the external part of the catheter. The lead 34' would be a stiff lead, capable of being driven rotationally, so as to pivot the lever 38 on it base in a clockwise direction, to slide the hatch 36 from a closed position, such as shown in FIG. 3c, to an open position, such as shown in FIG. 3d, relative to the port 20. When hatch 36 is open, as in FIG. 3d, the lead 34' may be rotated in a counterclockwise direction, to drive the lever 38 counterclockwise on its base, so that the lever will drive the hatch in a counterclockwise, transverse manner to slide the hatch 36 to a closed position, closing the port 20.

FIGS. 3e and 3f represent still another embodiment of port closure apparatus where an expandable balloon 40 is used to block or close the port 20, for example, when the balloon 40 is enlarged, for example, by inflation, as in FIG. 3f. When the balloon 40 is reduced in size, as in FIG. 3e, such as by deflation, for example, the port 20, and thus the bypass, will be open. The balloon 40 is connected to a lumen 22' which extends to the external portion of the catheter. The lumen 22' may be connected to a pump means at the external end of the catheter and, the balloon 40 may be inflated and/or deflated, using a pump means, as desired.

There has been shown and described a preferred embodiment of the invention, an improved balloon catheter with a bypass of the occluded segment of the catheter, mounted in the catheter. In addition, structure for effectively opening and closing the bypass in the balloon catheter has been shown and described. Alternate structure for the bypass and alternate structure for the bypass closure has been shown and described. Other changes and/or modifications in the invention may be made, as may become apparent to those skilled in the art, without departing from the invention as defined in the appended claims.

What is claimed is:

1. An improvement in a catheter, part of which is positionable in a blood vessel of a body having a blood flow therethrough, said catheter having a first expandable balloon and a second expandable balloon, expandable beyond a wall of said catheter, said first balloon and said second balloon spaced along said catheter for generating an occluded segment of said blood vessel between said first balloon and said second balloon when said first balloon and said second balloon are expanded, said improvement in said catheter comprising:

a first port in said wall of said catheter, said first port positioned upstream, in the direction of said blood flow from said first balloon;

a second port in said wall of said catheter, said second port positioned downstream, in the direction of said blood flow from said second balloon; and, a lumen within said catheter and having a first end and a second end, said first end connected to said first port and said second end connected to said second port for defining a bypass for blood in said blood flow for shunting said occluded segment of said blood vessels spaced and positioned for passing a portion of said blood from upstream in the direction of blood flow from said occlusion to downstream in the direction of blood from said occlusion.

2. An improvement in a catheter as in claim 1 and in which said first balloon is located upstream, in the direction of said blood flow from said second balloon.

3. An improvement in a catheter as in claim 1 and in which said improvement further includes a port closure means for closing said first port for closing said bypass.

4. An improvement in a catheter as in claim 1 and in which said second port defines a tip of said catheter.

5. An improvement in a catheter as in claim 3 and in which said port closure means is slidable longitudinally along said catheter from a first position to a second position.

6. An improvement in a catheter as in claim 5 and in which said first position of said port closure means closes said first port.

7. An improvement in a catheter as in claim 3 and in which said port closure means is slidable transverse to a line extending longitudinally along said catheter from a first position to a second position.

8. An improvement in a catheter as in claim 3 and in which said port closure means includes a third balloon located within said bypass and connected to a second lumen, said third balloon being capable of being inflated through said second lumen for closing said first port and capable of being deflated through said second lumen for opening said first port.

9. An improvement in a catheter postionable in a blood vessel of a body, said catheter, including a first balloon and a second balloon spaced from each other and including means for expanding said first balloon and said second balloon to a wall of said blood vessel for generating an occluded segment in said blood vessel between said first balloon and said second balloon when said first balloon and said second balloon are expanded, said improvement in said catheter comprising:

a first lumen within said catheter coupled to and opening into an interior of said first balloon for expanding and contracting said first balloon therethrough and independent of said second balloon, a second lumen within said catheter coupled to and opening into an interior of said second balloon for expanding and contracting said second balloon therethrough and independent of said first balloon, and a bypass for bypassing at least a portion of blood from upstream in the direction of blood flow of said occluded segment to downstream in the direction of blood flow of said occluded segment.

10. An improvement in a catheter as in claim 9 and said improvement in said catheter further comprises:

a first port in a wall of said catheter upstream, in the direction of blood flow through said blood vessel, from said first balloon;

a second port in said wall of said catheter downstream, in the direction of said blood flow through said blood vessel, from said second balloon; and a third lumen within said wall of said catheter having a first end and a second end and said first port defines said first end of said third lumen and said second port defines said second end of said third lumen.

11. An improvement in a catheter as in claim 10 and said improvement in said catheter further comprises a port closure means having an open port position and a closed port position and said port closure means is adjustable from said open port position to said closed port position.

12. An improvement in a catheter as in claim 10 and in which said second port defines an anterior end of said catheter.

13. An improvement in that part of a catheter which is positionable in a blood vessel of a body having a blood flow therethrough, said catheter having a first balloon and a second balloon, spaced from each other longitudinally along said catheter and expandable beyond a wall of said catheter to a wall of said blood vessel, said first balloon and said second balloon for generating an occluded segment in said blood vessel between said first balloon and said second balloon when said first balloon and said second balloon are expanded, said improvement in said catheter comprising:

a first port in said wall of said catheter, said first port positioned adjacent said first balloon and upstream, in the direction of said blood flow from said first balloon;

a second port in said wall of said catheter, said second port positioned adjacent said second balloon and downstream, in the direction of said blood flow from said second balloon, and, a lumen within said catheter and having a first end and a second end, said first end connected to said first port and said second end connected to said second port for defining a blood shunt in said catheter for bypassing said occluded segment of said blood vessel spaced and positioned for passing a portion of said blood from upstream in the direction of blood flow from said occlusion to downstream in the direction of blood from said occlusion.

14. An improvement in that part of a catheter as in claim 13 and wherein said improvement further comprises a port closure means adjustable from an open position to a closed position, said open position for opening said first port and for opening said blood shunt, said closed position for closing said first port and for closing said blood shunt.

* * * * *